United States Patent [19]
Nigam

[11] Patent Number: 5,976,163
[45] Date of Patent: Nov. 2, 1999

[54] APPARATUS FOR RESECTING CORNEAL TISSUE

[75] Inventor: Alok Nigam, Trabuco Canyon, Calif.

[73] Assignee: Bausch & Lomb Surgical, Inc., Rochester, N.Y.

[21] Appl. No.: 09/166,622

[22] Filed: Oct. 5, 1998

Related U.S. Application Data

[63] Continuation of application No. 08/566,838, Dec. 4, 1995, Pat. No. 5,817,115.

[51] Int. Cl.⁶ ...................................................... A61F 9/00
[52] U.S. Cl. ........................... 606/166; 606/167; 606/172
[58] Field of Search ..................................... 606/166, 167, 606/172, 174; 30/113, 278, 124

[56] References Cited

U.S. PATENT DOCUMENTS

| | | | |
|---|---|---|---|
| 3,882,872 | 5/1975 | Douvas et al. | 128/305 |
| 4,662,370 | 5/1987 | Hoffmann et al. | 128/305 |
| 5,342,378 | 8/1994 | Giraud et al. | 606/166 |
| 5,496,339 | 3/1996 | Koepnick | 606/166 |

*Primary Examiner*—Michael Buiz
*Assistant Examiner*—Daphna Shai
*Attorney, Agent, or Firm*—Akin, Gump. Strauss, Hauer & Feld, L.L.P.

[57] ABSTRACT

A cutting instrument for severing a thin layer of corneal tissue from the surface of the eye, preferably leaving a flap. The cutting instrument includes a body portion that forces the surface of the eye against an applanating surface through a vacuum. A blade with a cutting edge not perpendicular to the direction of travel is then urged across the surface of the eye, severing a thin layer of corneal tissue. The blade can then be retracted, the instrument removed, leaving a flap of corneal tissue suitable for surgical procedures to modify corneal curvature.

25 Claims, 9 Drawing Sheets

APPARATUS FOR RESECTING CORNEAL TISSUE

This application is a continuation of application Ser. No. 08/566,838, filed Dec. 4, 1995, issued as U.S. Pat. No. 5,817,115 on Oct. 6, 1998.

BACKGROUND OF THE INVENTION

1. Field of the Invention

The invention relates to an apparatus for and method of resecting corneal tissue, and more particularly to an apparatus for and method of resecting a thin corneal flap from the surface of the eye.

2. Description of the Related Art

Since the development of vision correcting lenses, ophthalmologists have continuously sought more permanent methods of correcting vision than glasses or contact lenses. Eye surgeons have tried, accepted, rejected, and modified various techniques in their quest for a simple, permanent procedure for correcting vision that retains its effectiveness over time and presents minimal side effects.

An early experimenter in the field was Jose I. Barraquer, who developed the technique of myopic keratomileusis. In this technique, the surgeon removes a lenticle, or corneal disk, from the corneal surface and affixes that corneal disk onto a cryolathe. The surgeon then reshapes the frozen disk, thaws the disk, and reattaches it to the stromal bed of the eye. Replacement of the reshaped disk results in a change of corneal curvature which in turn causes vision correction.

Barraquer also experimented with creating a flap on the surface of the cornea and then making a lamellar resection from the exposed stomal bed. The flap was then replaced, with the lamellar resection resulting in a flatter corneal curvature. This technique became known as in situ keratomileusis. The effectiveness of in situ keratomilcusis, however, was extremely sensitive to the accuracy of the lamellar resection taken from the stromal bed.

In both myopic keratomileusis using a cryolathe and in situ keratomileusis using a lamellar resection, the accuracy and depth of the cuts into the cornea of the eye were extremely important. Myopic keratomileusis required resection of a very uniform corneal disk, otherwise when the disk was turned on the cryolathe, the reshaping would cause irregularities in the ultimate vision correction. In situ keratomileusis was sensitive to the corneal cut for a different reason. The first cut had to be very even to form a uniform stromal surface from which to take the second resection. The second resection was even more sensitive to accuracy, because it was that resection that resulted in the vision correcting profile.

Because these techniques required such precise cuts, doctors and technicians developed a variety of extremely accurate cutting instruments known as microkeratomes. These instruments typically included a precisely aligned blade that was passed over the eye with its cutting edge perpendicular to the direction of travel. The blade was oscillated at high speed, preventing binding of the blade with the tissue being cut. The microkeratome was further modified and improved, for example, through the addition of micrometers and automatic advancement systems. This latter development, patented in U.S. Pat. No. 5,133,726 to Ruiz, et al., was necessary because the speed at which a microkeratome cuts the cornea was found to affect the thickness of the cut—again, of great importance in the early techniques.

While these techniques were maturing, a new laser device, the excimer laser, was making an impact in the field of eye surgery. This laser is a "cold" light laser, in that it breaks the molecular bonds through light rather than burning the tissue through heat. Because the excimer laser leaves surrounding tissue virtually unaffected, the excimer laser has become the preferred laser for operations on the cornea of the eye, and has been used in a number of techniques for removing tissue from the surface of the eye for correcting vision. An example for such a technique is found in PCT application PCT/EP93/02667 to Hohla.

The early Barraquer technique of in situ keratomileusis was greatly improved upon by Gholam Peyman, who married keratomileusis with the excimer laser. This technique is described in U.S. Pat. No. 4,840,175 to Peyman. The cornea is first resected, exposing the stromal tissue underneath. That exposed tissue is then ablated for refractive correction, and the corneal cap is replaced. This technique, known as laser in situ keratomileusis, has the advantage over "surface" based excimer laser techniques. These advantages in part flow from the structure of the eye itself. The cornea of the eye actually includes five layers, the outer three of which are illustrated in FIG. 1. The outer most layer is known is as the epithelium layer, denoted as layer 1 in FIG. 1, and is 50 to 90 microns thick. Bowman's membrane, denoted as layer 2, separates the epithelium from the substantiapropria, or stroma, layer 3. Bowman's membrane is about 12 microns thick. The stroma layer 3 makes up most of the thickness of the cornea, being from 400 to 450 microns thick.

Typical prior art excimer laser techniques first ablated away both the epithelium layer and Bowman's membrane before reaching the stroma layer. Peyman's technique instead provides for cutting into the stroma layer, then ablating the stroma layer, and then replacing that stroma layer. The end result is that neither the epithelium nor Bowman's membrane is affected. Peyman's technique eliminates trauma to the external surface layers of the cornea, resulting in improved healing and retained vision correction.

Peyman's technique has become known to ophthalmic surgeons as the "flap and zap" technique. To perform this technique, doctors typically use a microkeratome like those used for both myopic and in situ keratomileusis. While these microkeratomes, as noted above, are very precise instruments, they are also both expensive and unwieldy, and must be sterilized between uses. Further, they include high speed oscillating blades, as well as other complicated moving parts. It would be greatly desirable to simplify the resection of a corneal flap before performing the Peyman technique.

SUMMARY OF THE INVENTION

A cutting instrument according to the invention provides an apparatus for creating a corneal flap suitable for laser in situ keratomileusis. The cutting instrument according to the invention includes a body portion that has an eye receiving cavity and a blade guide that forms a path of blade travel intersecting the eye receiving cavity. A blade with a cutting edge non-perpendicular to the path of blade travel is forced along the blade guide by a plunger.

When the cutting instrument is placed on the eye, a vacuum is pulled through a vacuum port, causing the surface of the eye to be securely pulled into the eye receiving cavity and against an applanating surface formed by a centering lens. The plunger is then actuated, causing the blade to sever a portion of the flat surface of the eye in a slicing action, forming a corneal flap. Because the vacuum holds the flap securely against the applanating surface, any binding with the blade will not cause the flap to tear from the cornea; the flap instead stays securely centered. After the vacuum is released, the flap can then be pulled back for laser in situ keratomileusis of the exposed corneal tissue.

Further according to the invention, a thin layer of corneal tissue is severed from the surface of the eye using a blade traveling along a path of blade travel, but with a cutting edge not perpendicular to the path of blade travel, thus resulting in a slicing action as the blade cuts through the tissue.

Further, according to the invention, the blade is quickly urged into the eye and then retracted from the eye in a single, continuous motion. This is preferably done using a rotating cam mechanism in which the rotational motion is translated into a back and forth linear motion.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

The disclosed corneal resection instrument is especially suited for use in excimer laser in situ keratomileusis. It is simpler than standard microkeratomes used in eye surgery, it can be easily manufactured, and is inexpensive enough to be a disposable, single-use device, which eliminates the need for sterilization between procedures, and thus reduces the possibility of infection.

The disclosed instrument takes advantage of the unique requirements for creating a corneal flap for laser in situ keratomileusis. Microkeratomes developed for myopic keratomileusis or in situ keratomileusis faced stringent requirements of accuracy, reproducibility, and consistency of cuts. Further, the cut thickness of these complex instruments had to be adjustable.

These requirements, however, are somewhat relaxed in laser in situ keratomileusis. The depth of ablation is generally dependent only on the amount of laser radiant energy applied to a particular spot controlled by the number of laser shots.

Figure 1:
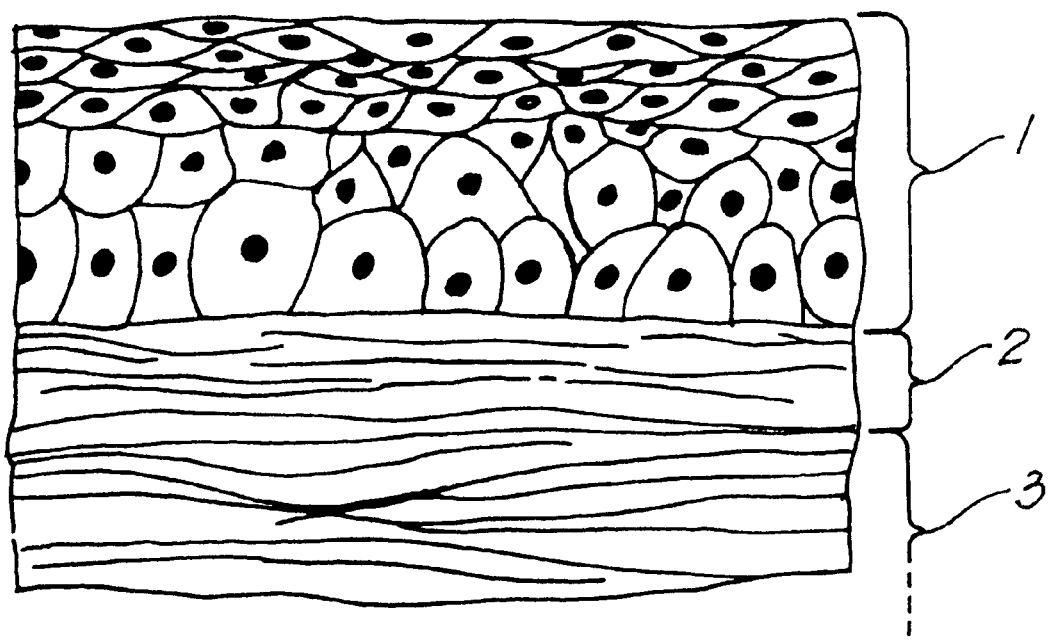
FIG. 1 is a cross-sectional view of the first three layers of tissue of the cornea of an eye.
Figure 2A:
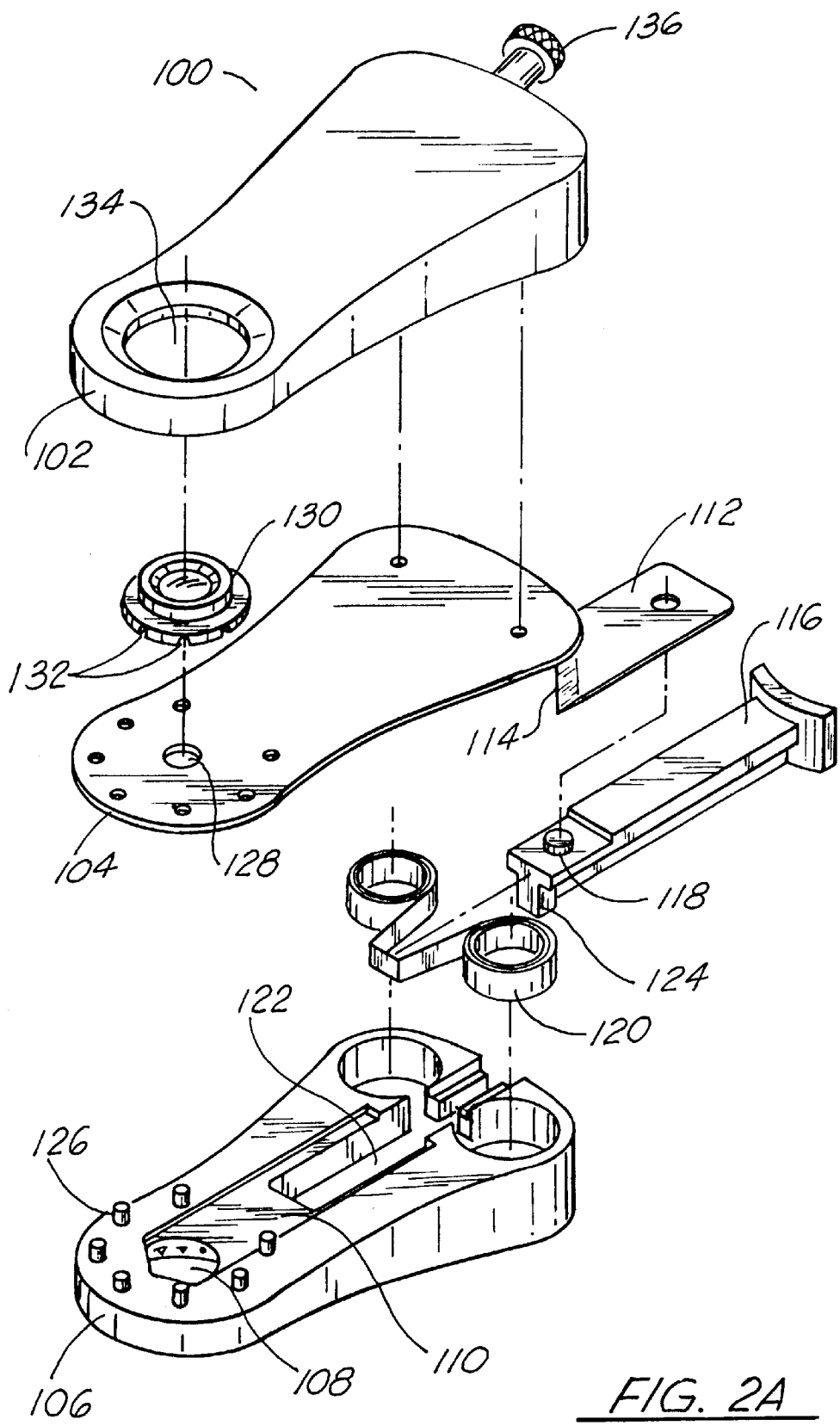
FIG. 2A is an exploded view of a cutting instrument according to the invention.

To this end, FIG. 2A illustrates an exploded view of an improved instrument for cutting corneal tissue by severing at least a portion of a thin layer of corneal tissue from the remainder of the eye. Shown is a disassembled view of a cutting instrument 100. The body of the cutting instrument 100 is formed from a cover 102, a sole plate 104, and a base 106. The cover 102 and the base 106 are preferably made from high impact plastic, while the sole plate 104 is preferably stainless steel.

The lower surface of the base 106 forms an eye receiving cavity 108. This eye receiving cavity 108 is generally spherically shaped so that it fits on a patient's eye. This eye receiving cavity 108 intersects with a blade guide 110, whose lower and side surfaces are formed by a recess within the base 106, and whose upper surface is bounded by the sole plate 104 when the cutting instrument is assembled. A blade 112 fits into the blade guide 110 when the cutting instrument 100 is assembled, such that the blade 112 moves along a path of blade travel defined by the blade guide 110. The blade 112 further includes a blade edge 114, which is diagonal relative to the path of blade travel. The diagonal orientation of this blade edge 114 assists the cutting instrument 100 in severing a portion of the cornea of the eye without the need to oscillate the blade 112, as was necessary in prior microkeratomes.

A plunger 116 is used to urge the blade 112 along the path of blade travel and across the eye receiving cavity 108. The plunger 116 is preferably made of a high impact plastic, and includes a peg 118 for fit mounting the blade 112. When the cutting instrument 100 is assembled, the sole plate 104 keeps the blade 112 securely mounted on the peg 118. The plunger 116 and a symmetrical spring 120 are disposed within a plunger recess 122 in the base 106. The plunger recess 122 includes two circular openings for the symmetrical spring 120, and when assembled, the spring 120 forces both the plunger 116 and the blade 112 into a retracted position away from the eye receiving cavity 108. To prevent the spring 120 from fully expelling the plunger 116 from the cutting instrument 100, the plunger 116 further includes a stop wall 124, which abuts against a similar wall within the base 106 in its at-rest position.

The spring 120, the plunger 116, and the blade 112 are inserted into the plunger recess 122, and then the sole plate 104 is mounted on top of the base 106. Thus, the sole plate 104 forms a top surface for the blade guide 110. The plunger 116 is then used to urge the blade 112 along the path of blade travel defined by the blade guide 110, and across the opening in the eye receiving cavity 108. The blade 112 is stopped by the blade 112 striking an end of the blade guide 110, as is further discussed below in conjunction with FIG. 3, although a number of types of stops could instead be used. Pegs 126 are used to align the base 106 with the sole plate 104 and the cover 102.

The sole plate 104 includes a resection aperture 128 that defines the boarder of the ultimately cut corneal cap. A transparent centering lens 130 with a flat undersurface is placed atop this resection aperture 128, and is held in place by a centering aperture in the cover 102, and radial vacuum ports 132 in the centering lens 132 are ultimately used to force the surface of the eye flush against the flat undersurface of the centering lens 130. In this context one can understand the function of the resection aperture 128. The sole plate 104 is preferably about the thickness of the desired corneal flap. So, when an eye is placed within the eye receiving cavity 108, and a vacuum is applied to the radial vacuum ports 132, the surface of the eye E is forced against the flat undersurface (an applanating surface) of the centering lens 130, and thus a thickness of cornea approximately the thickness of the sole plate 104 is forced above the undersurface of the sole plate 104. Then, when the blade 112 is urged by the plunger 116 along the blade guide 110, a corneal flap is cut from the surface of the eye. This is all further discussed below in conjunction with FIGS. 2B through 5.

The surface of an eye within the eye receiving cavity 108 is pulled flush with the applanating surface formed by the centering lens 130 by a vacuum drawn on a vacuum port 136 in the cover 102. This vacuum port 136 is preferably a Luer fitting, and can be connected to a variety of sources of vacuum, such as a mechanical vacuum pump, a syringe, or a wide variety of other vacuum sources. A vacuum drawn on the vacuum port 136 correspondingly draws a vacuum on the radial vacuum ports 132 of the centering lens 130 through a series of ports within the cover 102, which are discussed below in conjunction with FIG. 2B.

A variety of techniques can be used to secure the cutting instrument 100 into one operable assembly. Adhesives, mechanical connectors such as bolts, or ultrasonic welding are just three possibilities. One of ordinary skill in mechanical arts would appreciate the many options available.

Figure 2B:
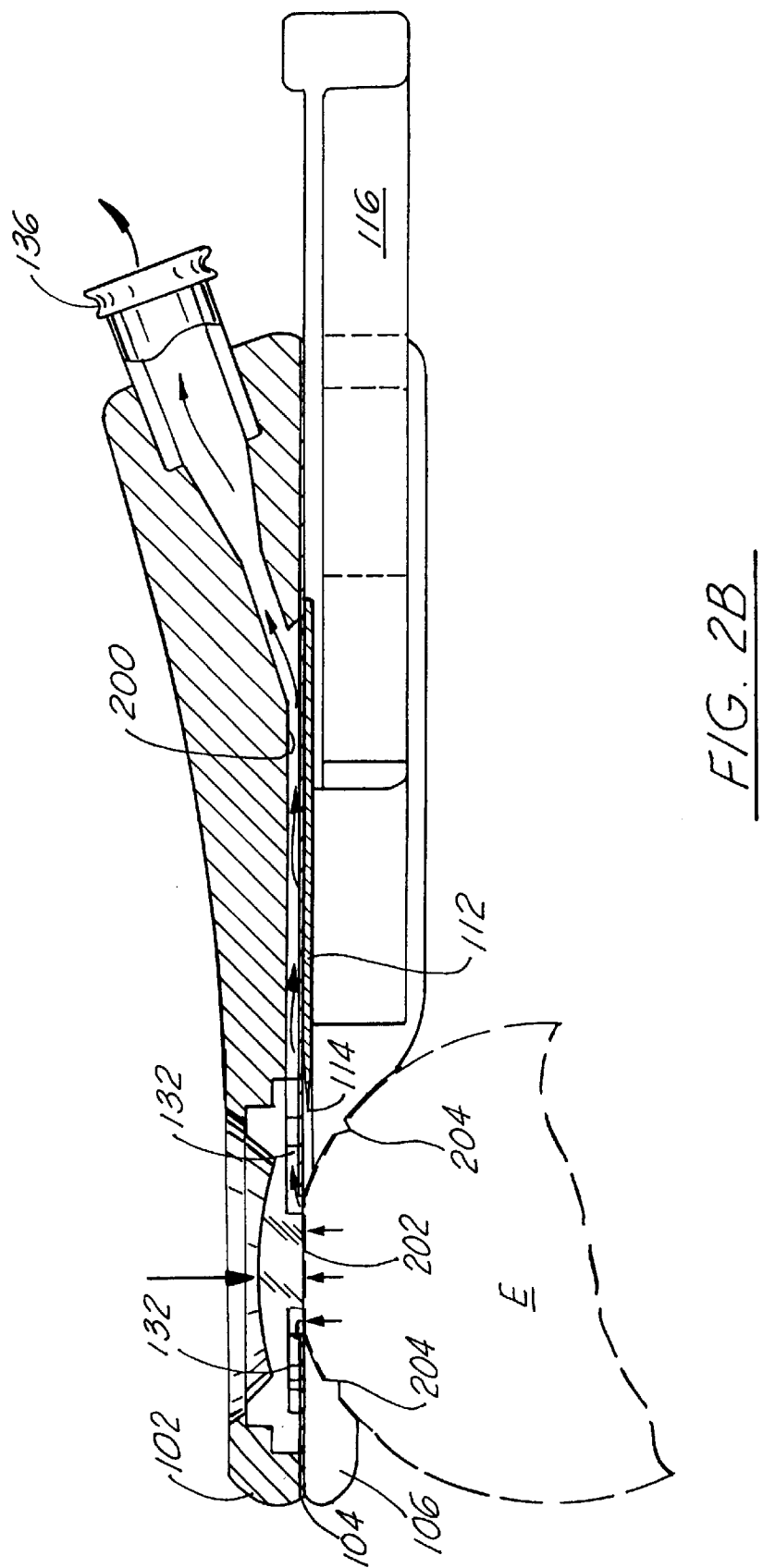
FIG. 2B is a cutaway side view of the cutting instrument of FIG. 2A, showing the cutting instrument used in conjunction with an eye.

FIG. 2B illustrates the use of the cutting instrument 100 in conjunction with an eye E. When a vacuum is applied to the vacuum connection 138, a vacuum is drawn through a vacuum port 200 formed by the cover 102 and the sole plate 104. This vacuum is further drawn through the radial vacuum ports 132, which are further illustrated below in conjunction with FIG. 3. This vacuum pulls the surface of the eye E flush against the underside of the centering lens 130, which forms an applanating surface 202. Although the applanating surface 202 is shown to be flat, it could have a slight concave, or possibly even convex, curvature. The plunger 116 then forces the blade 112 to sever a portion of the cornea of the eye E.

Further, when the plunger is activated and then retracted, at all times the lens cap formed against the applanating surface 202 is held in place by the vacuum. The vacuum, pulled through the vacuum port 136, helps prevent the very thin corneal cap from being torn from the surface of the eye, even when the blade 112 is retracted.

As is further discussed below in conjunction with FIGS. 11–13, the thickness of the corneal cut is determined not only by the thickness of the sole plate 104, but also by the angling of the blade edge 114.

FIG. 2B also illustrates the use of small projections 204 within the eye receiving cavity 108. These small projections 204 embed themselves within the surface of the eye E, preventing the cutting instrument 100 from slipping when the blade 112 cuts the eye E. These small projections 204 are preferably sharp enough to penetrate the sclera for added control.

Figure 3:
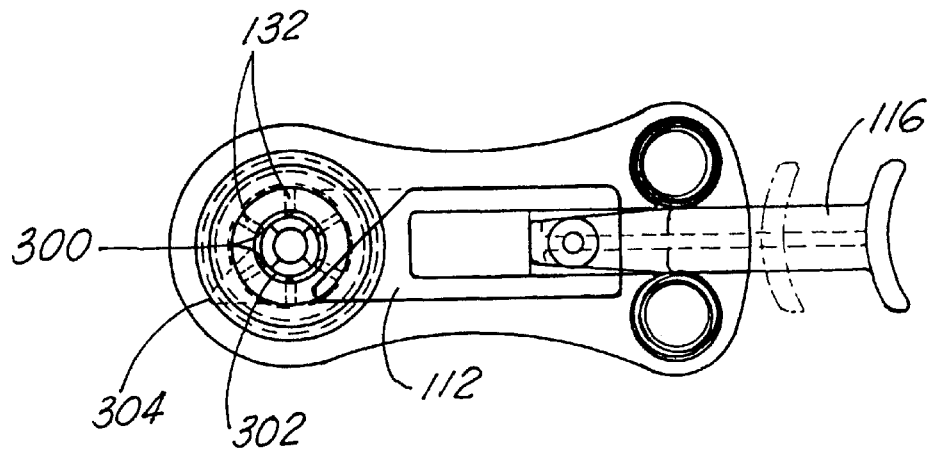
FIG. 3 is a cutaway top view of the cutting instrument of FIG. 2A.
Figure 4:
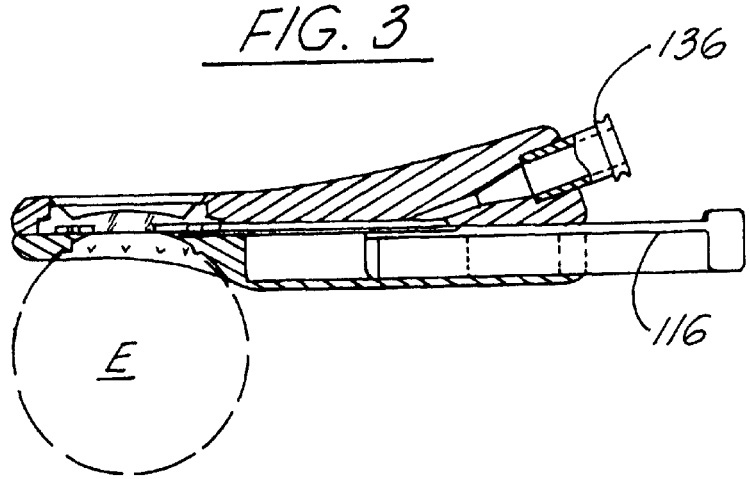
FIG. 4 is another cutaway side view of the cutting instrument of FIG. 2A.

FIGS. 3 and 4 show top and side views of the cutting instrument 100 of FIG. 2A. FIG. 3 shows further details of the radial vacuum ports 132 around the centering lens 130, as well as the extent of travel of the blade 112 and the plunger 116. Six of the radial vacuum ports 132 are formed in the body of the centering lens 130, and these radial vacuum ports 132 slightly overlap the resection aperture 128 in the sole plate 104. These slight overlaps form six vacuum orifices 300 through which the vacuum draws the eye E against the applanation surface 202 formed by the centering lens 130. The radial ports 132 are otherwise sealed by the sole plate 104.

Although six radial ports 132 are shown for forcing the cornea against the applanating surface 202, preferably a highly perforated disc would be used, so that the vacuum would uniformly draw the eye E against the applanating surface 202 with the vacuum distributed over the entire area of the cornea held against that surface 202.

FIG. 3 also illustrates the final position of the blade 112 when actuated, as well as the slicing effect of the blade edge 114. The blade 112 hits a blade stop 304 at its end of travel, leaving an approximately 1 millimeter hinge of tissue connecting the corneal flap with the cornea itself. This hinge is located in the space between the blade edge 114 and the edge of the resection aperture 128. Instead of a blade stop 304, the blade stop could extend substantially along the edge of the blade 114, so that the blade edge 114 strikes the stop along its length substantially simultaneously. Further, the range of motion of the plunger 116 could instead be limited.

FIG. 3 further shows that the centering lens 130 includes a reticle 302 for assisting the surgeon in centering the centering lens 130 on the eye when the cutting instrument 100 is placed on the eye.

To use the cutting instrument 100, the surgeon places the cutting instrument 100 over the eye E, and centers the reticle 302 over the center of the eye E. The surgeon then applies a vacuum to the vacuum port 136, causing the surface of the cornea of the eye E to be pulled flush with the applanating surface 202 of the centering lens 130. The surgeon urges the plunger 116 forward until it hits the blade stop 304. At this point, the 1 millimeter hinge of tissue remains connecting the flap of the cornea to the cornea of the eye E itself. This flap is formed at a location near the top left corner of the reticle 302 seen in FIG. 3. The plunger 116 is then returned to its initial position by the spring 120. At this point, the vacuum pulled through the vacuum orifices 300 prevents the corneal cap from sticking to the surface of the blade 112 and tearing.

The surgeon then releases the vacuum on the vacuum port 136 and removes the cutting instrument 100. The surgeon then pulls the flap of corneal tissue away from the center of the eye E so that the surgeon can then perform excimer laser surgery on the exposed underlying surface of the stromal bed of the cornea. After excimer surgery, the surgeon replaces the flap of corneal tissue, completing the laser in situ keratomileusis procedure.

Although a manual plunger 116 is shown, the blade 112 can be actuated by another source of energy or forward motion, such as hydraulic systems, step motors, screw drives, magnetic drives, etc. Preferably, however, a spring mechanism is used, as is described in FIGS. 17A and 17B.

Figure 5:
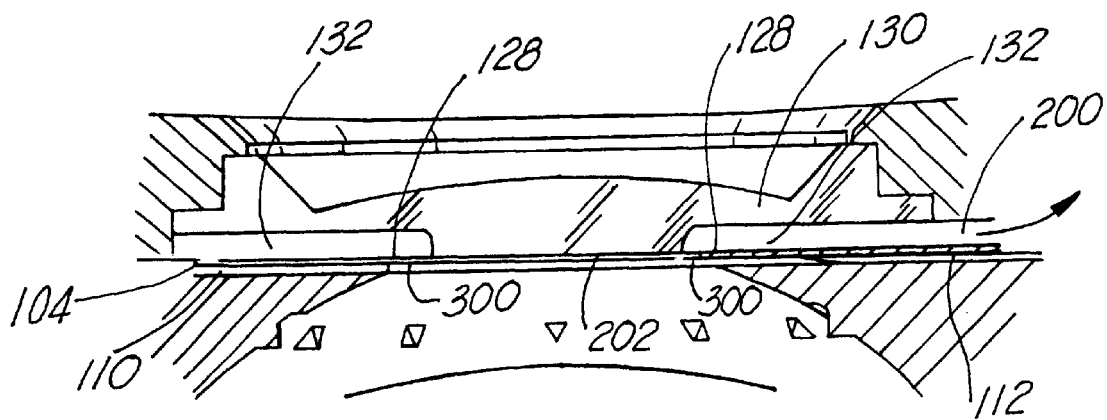
FIG. 5 is a magnified cutaway side view of the centering lens, the eye receiving cavity, the cutting blade, and the sole plate of the cutting instrument according to FIG. 2A.

FIG. 5 is a close up cutaway view of the centering lens 130, the sole plate 104, the blade guide 110, and the blade 112 illustrating the applanating surface 202 formed under the centering lens 130 as well as the radial vacuum ports 132, which force the surface of the eye E against the applanating surface 202.

When a vacuum is pulled on the radial vacuum ports 132, the surface of the eye E is pulled against the applanating surface 202 of the centering lens 130. This applanating surface 202 is a circular area defined by the area of the resection aperture 128 in the sole plate 104. This sole plate 104 is extremely thin and preferably forms a 150 micron spacer between the blade 112 and the applanating surface 202. The blade 112 is shown to be a single edged blade, with the flat portion of the blade 112 towards the applanating surface 202. Thus, when the plunger 116 is pushed, the cornea is cut to a depth of approximately 150 microns because the distance between the applanating surface 202 and the blade edge 114 is 150 microns. In this way, a 150 micron deep corneal flap is formed. The sole plate 104 could of course be of other thicknesses.

Although a specific configuration of vacuum ports and orifices is shown in the disclosed embodiment, one can readily appreciate that a wide variety of differing configurations of vacuum ports can instead be used. As long as a vacuum is used to securely pull the surface of the eye against an applanating surface, the exact configuration of ports to provide that vacuum is not critical.

Figure 6:
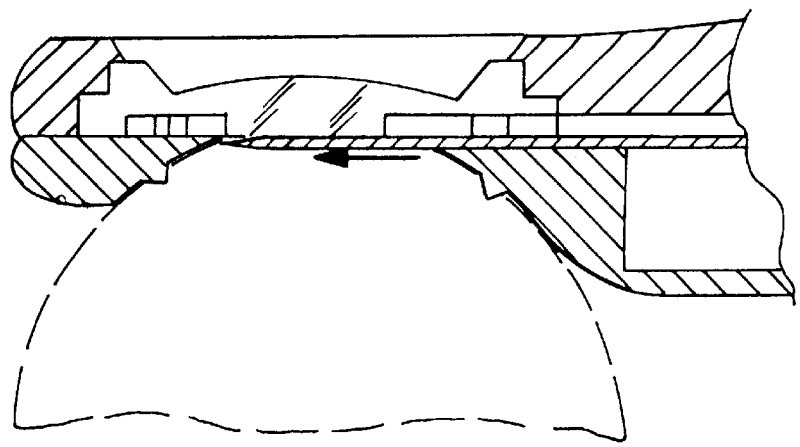
FIG. 6 is a cutaway side view showing the cutting instrument of FIG. 2A in use.

Turning to FIG. 6, the blade 112 is shown in its fully extended position, removing a flap of corneal tissue from an eye E. In this position, a flap is severed equal in thickness to the distance of the applanating surface 202 from the blade edge 114.

Figure 7:
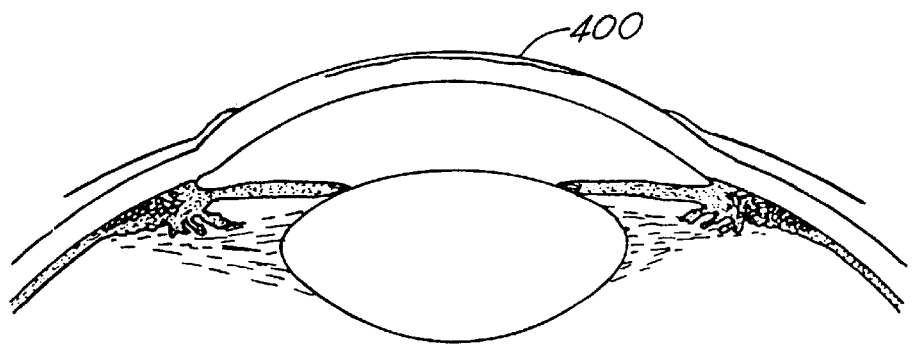
FIGS. 7 and 8 are cutaway side views of an eye illustrating a corneal flap created by the cutting instrument according to the invention.

The results of such a cut are shown in FIG. 7, which shows a severed flap 400 of corneal tissue. Although the cut of the flap 400 appears to be curved in FIG. 7, this is because the normally curved surface of the cornea was flattened against the applanating surface 202 when a vacuum was drawn on the vacuum port 136. Thus, a generally uniform depth of corneal tissue was resected, which then formed a curved shape once the vacuum was released.

Figure 8:
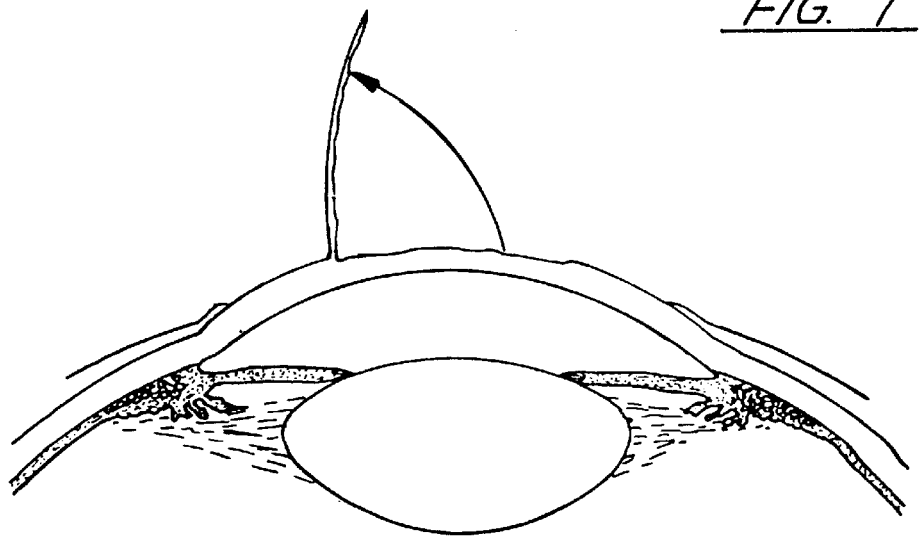

In practice, once the corneal flap 400 is formed, it is then pulled back, as illustrated in FIG. 8, in preparation for excimer laser surgery. The exposed surface of the cornea is then ablated, such as is described in U.S. Pat No. 4,840,175 to Peyman. A wide variety of techniques can be used for this ablation, to correct for such various conditions as myopia, hyperopia, astigmatism, and even irregular astigmatism. The resected flap is then returned to its original position, where it can either be sutured or left unsutured for healing.

Figure 9:
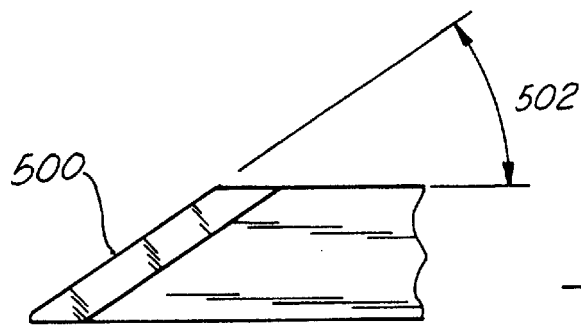
FIG. 9 is a top view of a diagonal cutting blade for use with the cutting instrument according to invention.
Figure 10:
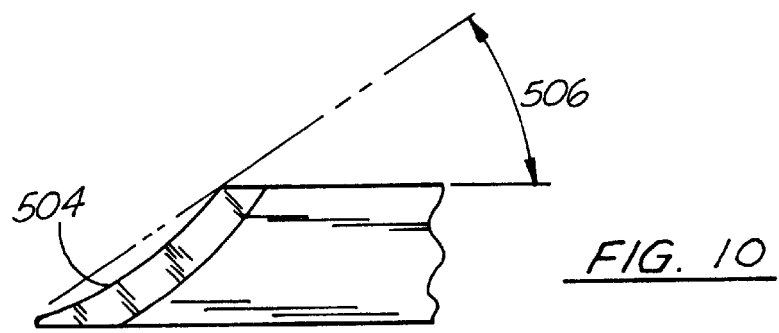
FIG. 10 is a top view of a crescent shaped diagonal cutting blade for use with the cutting instrument according to the invention.

FIGS. 9 to 13 illustrate a number of blade configurations. FIGS. 9 and 10 are top views of the blade 112, illustrating the diagonal nature of the blade 112. In FIG. 9, blade 112 has a straight cutting edge 500 that forms an angle 502 to the path of blade travel. In FIG. 10, a curved cutting edge 504 is shown, again forming an angle 506 to the path of blade travel. The diagonal angle of attack 502 and 504 of the cutting blade greatly simplifies the cutting instrument 100. Typical microkeratomes use perpendicular blades that oscillate at a very high frequency to prevent binding between the cornea and the keratome blade. According to the invention, however, the diagonal cutting edges 500 and 504 need not be oscillated. The diagonal cutting edges 500 and 504 instead provide a "slicing" action as the blade 112 is urged into the corneal tissue. In this way, the need for oscillating is removed, along with the associated hardware.

Figure 11:
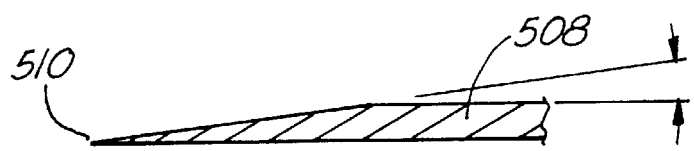
FIGS. 11 through 13 are cutaway side views of blades for use with the cutting instrument according to the invention illustrating the angle of attack of the edges of the blades.
Figure 12:
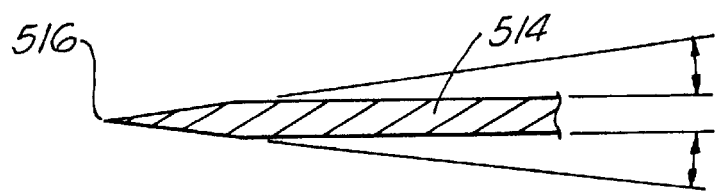
Figure 13:
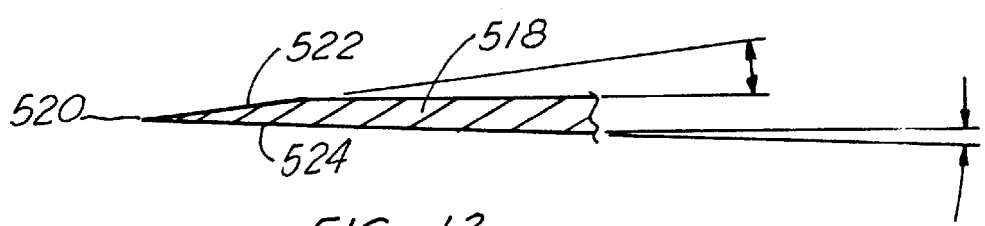

Turning to FIGS. 11 to 13, side views of various possible blade configurations are illustrated. FIG. 11 is a single-sided blade 508, with a blade edge 510 being formed by an inclined plane extending away from the blade edge 510 to the top surface of the blade. FIG. 12 is instead a double-sided blade 514, with the blade edge 516 being formed by two inclined planes extending towards both surfaces of the blade 514. Finally, FIG. 13 illustrates a double-inclined plane 518, where an upper surface 522 has a higher angle of attack than a lower surface 524.

Preferably, if the cutting edge 114 of the blade 112 is two-sided, such as shown in FIGS. 12 and 13, the inclination of each surface is approximately 0° to 30° from the surface plane of the blade 112. In the preferred configuration, only one side of the edge has an angular inclination, as illustrated in FIG. 11, and that inclination is 20° or less, and preferably 9°. The other side is parallel to the blade 112, thus creating a chisel edge. This chisel edge is then preferably placed within the cutting instrument 100 such that the edge with the angular inclination is away from the applanating surface 202. In this configuration, the blade 112 is then guided along the sole plate 104 when the plunger 116 is activated. If the chisel edge is instead placed so that the edge is away from the applanating surface 202, the blade would principally be guided along the base 106 along the blade guide 110.

Figure 14:
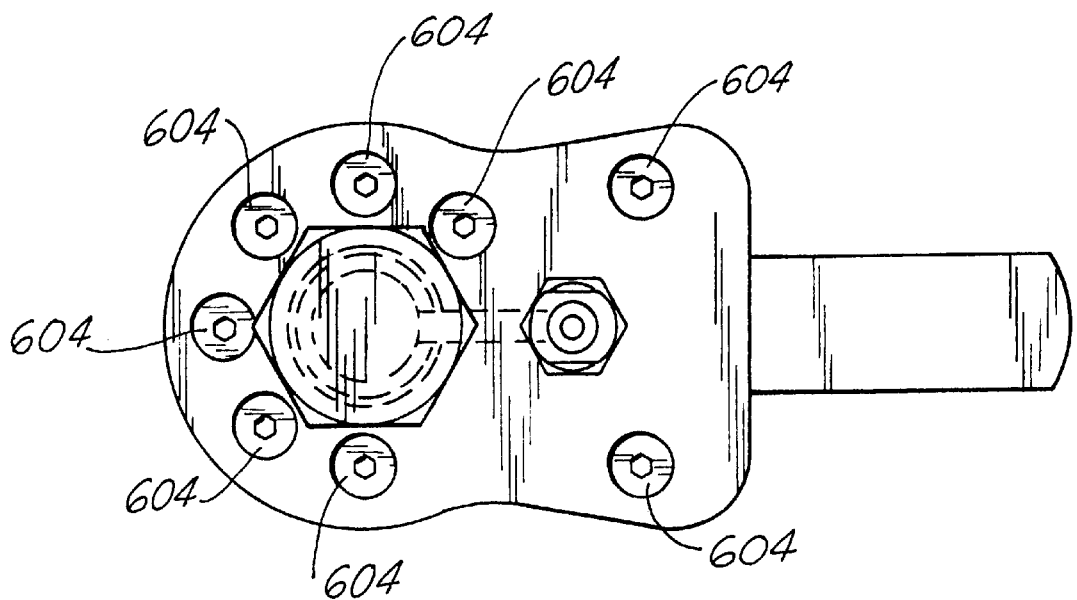
FIGS. 14 and 15 are top and side views of an alternative embodiment of the instrument of FIG. 2A.
Figure 15:
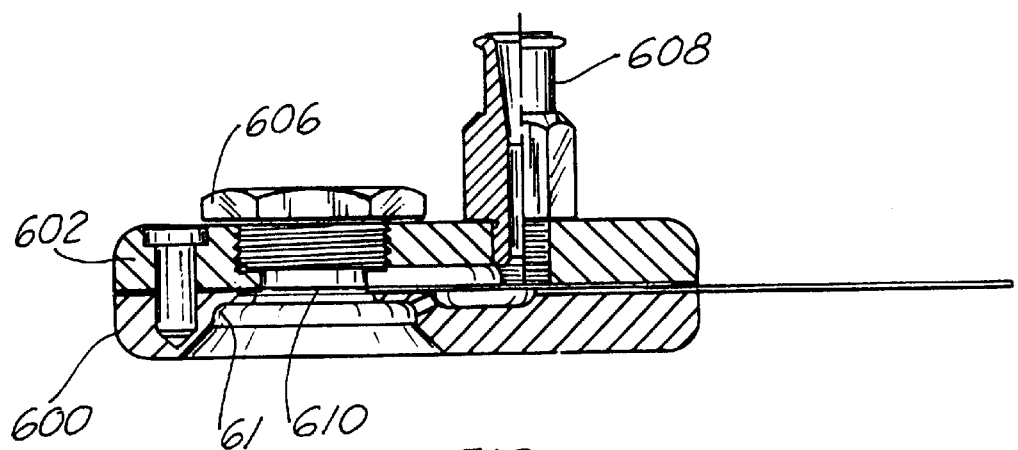

FIGS. 14 and 15 show a top and side view of an alternative embodiment of the cutting instrument according to the invention. This embodiment also includes a base 600 and a cover 602, but these two elements are bolted together with bolts 604. Further, a centering lens 606 is included, but is screwed into the top of the cover 602. By adjusting the depth to which the centering lens 606 is screwed, the depth of cut for the corneal flap can be altered.

This embodiment also includes two suction points for its vacuum port 608. As in the previous embodiment, the vacuum forces the surface of an eye flush against an applanating surface 610. Further, however, the vacuum is ported to a suction ring 612, providing a solid connection between the patient's eye and the base 600.

Figure 16:
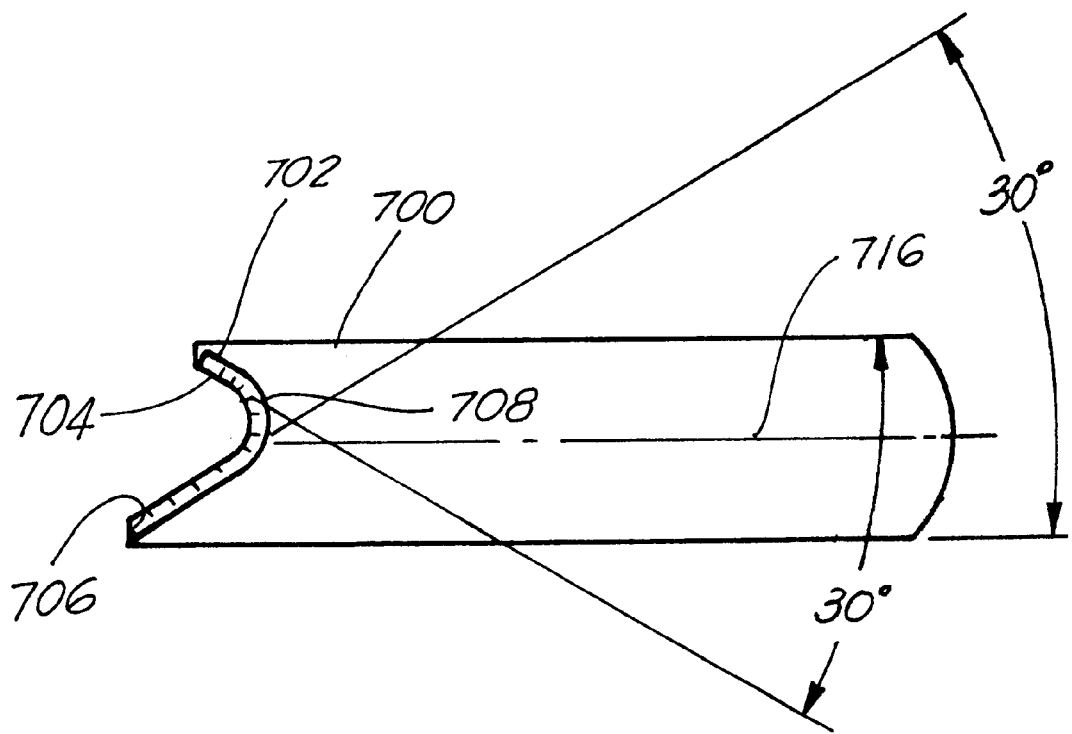
FIG. 16 is an alternative blade design for use in the instrument of FIG. 2A.

Turning to FIG. 16, illustrated is an additional blade design according to the invention that provides for simultaneous cutting from both sides of the cornea, resulting in a flap that is aligned along the axis of blade travel. That is, using a blade 700 according to FIG. 16, one can create a hinge in the severed tissue that (referring to FIG. 3) is formed at the nine o'clock position, which is aligned with the direction of blade travel, instead of being offset toward the eleven o'clock position, as would occur when using the blade and mechanism illustrated in FIG. 3. This can help avoid tearing of the cornea once the flap is created. The blade 700 includes edge 702 with an upper diagonal portion 704 and a lower diagonal portion 706. The lower diagonal portion 706 is slightly longer, and is first to engage the cornea when the blade 700 is used for cutting the eye. Through its slicing action, the lower diagonal portion 706 first cuts the cornea, and then the upper diagonal portion 704 contacts the cornea and begins slicing the cornea, also with a diagonal cutting action. Toward the end of the cut, a curved portion 708 of the edge 702 does not cut through the cornea, but instead leaves a flap.

Generally, the difficulty with cutting the cornea using keratomes is encountered on the initial cut. By first engaging the cornea with a slicing action, the cut into the cornea is already occurring by the time the curved portion 708 of the blade 700 encounters the cornea. Therefore, one achieves a slicing action leaving a small flap. Preferably, the angle of the upper diagonal portion 702 and lower diagonal portion 706 as illustrated is 30° offset from the path of blade travel indicated by an axis 716.

Figure 17A:
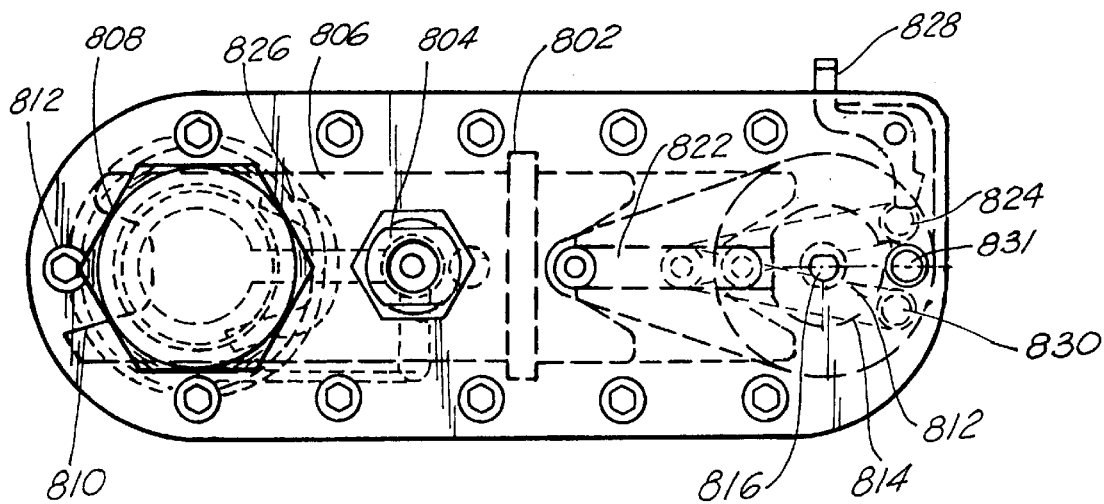
FIGS. 17A and 17B are top and side views of the further alternative design of FIGS. 14 and 15, further using a spring mechanism to cause the blade to quickly sever and then retract from the cornea.
Figure 17B:
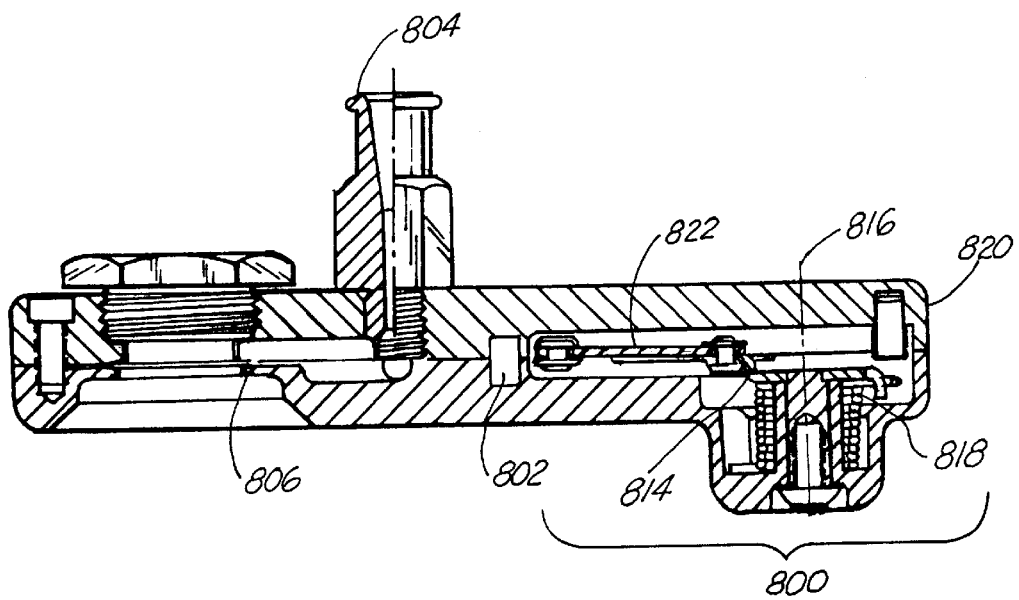

Turning to FIGS. 17A and 17B, a modified version of the instrument of FIGS. 14 and 15 is shown. The instrument is generally the same as that illustrated in FIGS. 14 and 15, except for an extended portion 800 that provides a rotating cam mechanism to quickly force the blade into and then back out of the cornea. Referring to both FIGS. 17A and 17B, a seal 802 is provided for allowing a vacuum to be built up through a vacuum port 804, similar to the vacuum port 608 in FIGS. 14 and 15. A blade 806 is also provided, slightly different from the previous blades in that the blade 806 has two diagonal portions 808 and 810, but the portion corresponding to the curved portion 708 of FIG. 16 is now a straight portion 812.

As previously discussed, the speed of cut is of particular importance when slicing the cornea. To that end, a cam mechanism 812 is used. A rotating disc 814 is mounted on an axis 816, and is surrounded by a spring 818. This spring 818 is engaged with both a body 820 of the instrument as well as with the rotating disc 814.

A connecting link 822 is also provided, illustrated in its fully blade-engaged position, which occurs halfway through the rotation of the disc 814. The connecting link 822 is attached to the disc 814 and the blade 806, thus translating the rotational motion of the disc 814 to linear motion of the blade 806. From a starting position 824, the blade is retracted as illustrated by the outline of the blade 826. Then, a locking lever 828 is released, and the spring 818 rotates the disc 814 very quickly from the start position 824 to a stop position 830, where the disc 814 is stopped by an elastomer bumper 831. During that rotation, the connecting link 822 forces the blade 806 into the cornea of the eye until it reaches the halfway position, at which point the rotation of the wheel pulls the blade out of the cornea until fully retracted, indicated by the stop position 830. In this way, a cut is quickly made, with a reproducible amount of force, and at a reproducible speed. This reproducible cutting action results in a uniform corneal flap, allowing a variety of surgeries to then take place.

Further, as will be apparent, a variety of mechanisms could be used to translate the rotational motion into linear motion. For example, the spring 818 could be directly connected to the connecting link 822, eliminating the disc 814. Further, other spring-based mechanisms could be used, such as two counter springs—one of which forces the blade into the cornea and the other of which then forces the blade out.

The foregoing disclosure and description of the invention are illustrative and explanatory thereof, and various changes in the size, shape, materials, and components, as well as in the details of the illustrated devices and construction and methods of operation may be made without departing from the spirit of the invention.

What is claimed is:

1. An instrument for severing at least a portion of a layer of corneal tissue from the remainder of an eye, which can be moved to expose underlying tissues, comprising:

a body portion which has a surface defining an eye-receiving cavity for receiving an eye;

a blade with a cutting edge for cutting corneal tissue;

a blade guide defining a path of blade travel towards the eye receiving cavity, the guide being positioned so that the path of blade travel intersects at least a portion of the cavity;

the blade having a cutting edge, the cutting edge not oriented along any direction of blade motion, and the blade being operatively moveable along the path of blade travel of the guide for severing at least a portion of a thin layer of corneal tissue from an eye received in the cavity.

2. The instrument of claim 1, wherein the body portion includes a vacuum connection communicating with the cavity, whereby when a vacuum is applied through the vacuum connection, an eye received in the cavity will be pulled into contact with an inner surface of the cavity.

3. The instrument of claim 2, wherein the inner surface includes a generally flat portion for flattening a portion of the eye when it is pulled into contact with the inner surface.

4. The instrument of claim 3, wherein the path of blade travel is oriented to be spaced a predetermined distance from and parallel to the generally flat portion.

5. The instrument of claim 4, wherein the body portion includes upper and lower portions that can be operatively connected, the lower part including a surface that defines a portion of the cavity that opens adjacent to the upper portion, and the upper portion includes a surface that defines a portion of the cavity and includes the flattened portion and opens adjacent to the lower portion, whereby surfaces of the upper and lower portions form the eye-receiving cavity when the portions are connected.

6. The instrument of claim 5 and further including a pathway formed between the upper and lower portions communicating with both the cavity and the vacuum connection.

7. The instrument of claim 5 and further including a slot formed in the lower portion defining the blade guide.

8. An instrument for severing at least a portion of a layer of corneal tissue from the remainder of an eye, which can be moved to expose underlying tissues, comprising:

a body portion which has a surface defining an eye-receiving cavity for receiving an eye;

a blade with a cutting edge for cutting corneal tissue; and a blade guide defining a path of blade travel, the guide being positioned so that the path of blade travel intersects at least a portion of the cavity, the blade having a cutting edge not oriented along any direction of blade motion and being operatively moveable along the guide for severing at least a portion of a thin layer of corneal tissue from an eye received in the cavity, wherein the surface defining the cavity includes a stop adapted to prevent the blade from traveling across the cavity and severing the layer of corneal tissue from the eye.

9. The instrument of claim 1, wherein the blade includes upper and lower flat surfaces and the cutting edge is formed between one of the flat surfaces and an inclined surface extending between the flat surfaces at an acute angle relative to said one of the flat surfaces.

10. The instrument of claim 1, wherein the blade includes upper and lower flat surfaces and the cutting edge is formed at the intersection between a pair of inclined surfaces extending at obtuse angles from the flat surfaces, and wherein the cutting edge is oriented diagonally relative to the path of blade travel.

11. The instrument of claim 1, wherein the cutting edge of the blade is straight.

12. The instrument of claim 1, wherein the cutting edge of the blade is concave.

13. The instrument of claim 1, further comprising a spring adapted to normally urge the cutting edge away from the cavity, which can be overcome when the cutting edge is pushed toward the cavity for engaging the corneal tissue.

14. The instrument of claim 13, wherein the plunger is connected to the blade and the spring engages the plunger.

15. The instrument of claim 1 further comprising:
means for quickly forcing the blade across the cavity and then retracting the blade from the cavity.

16. The instrument of claim 15, wherein said means comprises a spring-driven mechanism adapted to translate the spring's rotational motion into a linear motion when the blade is forced across the cavity and when the blade is retracted from the cavity.

17. An instrument for severing at least a portion of a layer of corneal tissue from the remainder of an eye, which can be moved to expose underlying tissues, comprising:
a body portion which has a surface defining an eye-receiving cavity for receiving an eye;
a blade with a cutting edge for cutting corneal tissue; and
a blade guide defining a path of blade travel, the guide being positioned so that the path of blade travel intersects at least a portion of the cavity, the blade having a cutting edge not oriented along any direction of blade motion and being operatively moveable along the guide for severing at least a portion of a thin layer of corneal tissue from an eye received in the cavity,
wherein the surface defining the cavity further includes a plurality of fixation spikes projecting from the surface adapted to hold the eye to prevent rotational movement relative to the cavity.

18. A keratome for making lamellar slices of tissue, particularly in a cornea of an eye, the keratome comprising:
a body portion formed of an upper half and a lower half, the lower half including an aperture forming walls of an eye receiving cavity, the upper half including a fixed applanation surface forming the base of the eye receiving aperture and including a vacuum duct to the eye receiving aperture, whereby when the eye receiving cavity is placed on the eye and a vacuum is applied to the vacuum duct, the surface of the eye is forced into substantially level contact with the applanation surface;
the upper and lower half forming a blade receiving guide to allow travel of a blade, the blade receiving guide extending away from the eye receiving aperture on a plane substantially parallel with said applanation surface; and
wherein the blade comprises a cutting edge is not oriented along any direction of blade motion.

19. The keratome of claim 18, further comprising a blade inserted in the blade receiving guide.

20. A method of severing at least a portion of a thin layer of corneal tissue from an eye, so that underlying tissue can be exposed, comprising the steps of:
placing an instrument on the eye, whereby the eye is received in a cavity defined by a surface of the instrument;
applying a vacuum to the eye through the instrument for maintaining the eye against the surface defining cavity;
moving a blade along a travel path towards the cavity where the travel path intersects at least a portion of the cavity for cutting at least a thin layer of corneal tissue from an eye in the cavity;
on the blade, providing a cutting edge not oriented along any direction of blade motion; and
retracting the blade outside the cavity.

21. The method of claim 20, wherein the step of applying a vacuum further includes maintaining the eye against a flattened portion formed on the surface that defines the cavity.

22. The method of claim 21, wherein the step of moving the blade further includes moving the blade along a path parallel to the flattened portion.

23. The method of claim 20, wherein the step of moving the blade further comprises a user engaging a plunger and manually pushing the blade to overcome resistance imparted by a spring for engaging the corneal tissue.

24. The method of claim 23, wherein the step of retracting the blade further includes the spring urging the blade back to its initial position.

25. A method for severing at least a portion of a thin layer of corneal tissue from an eye, so that underlying tissue can be exposed, the method comprising:
placing an instrument on the eye, whereby the eye is received in a cavity defined by a surface of the instrument;
applying a vacuum to the eye through the instrument for maintaining the eye against the surface defining the cavity; and
moving a blade along a travel path that intersects at least a portion of the cavity for cutting at least a thin layer of corneal tissue from an eye in the cavity, the blade having a cutting edge not oriented along any direction of blade motion;
retracting the blade outside the cavity,
wherein applying the vacuum further includes maintaining the eye against a flattened portion formed on the surface that defines the cavity,
wherein moving the blade further includes moving the blade along a path parallel to the flattened position, and
wherein moving the blade further includes moving the blade until it contacts a stop formed on the surface defining the cavity adapted to prevent the blade from moving across the entire width of the cavity.

* * * * *